United States Patent [19]

Stockhammer et al.

[11] Patent Number: 5,731,459
[45] Date of Patent: Mar. 24, 1998

[54] PROCESS FOR SEPARATING AMINO ACIDS AND AMINOSULPONIC ACIDS THROUGH ADSORPTION ON ZEOLITES

[75] Inventors: Stefan Stockhammer, Freigericht; Wiltrud Schäfer-Treffenfeldt, Obertshausen; Günter Knaup, Bruchkobel; Karlheinz Drauz, Freigericht; Elfriede Sextl, Geiselbach, all of Germany

[73] Assignee: Degussa Aktiengesellschaft, Frankfurt, Germany

[21] Appl. No.: 704,976

[22] Filed: Aug. 28, 1996

[30] Foreign Application Priority Data

Sep. 26, 1995 [DE] Germany ............ 195 35 751.5

[51] Int. Cl.⁶ ............ C07C 51/48; C07C 51/487; C07C 227/28; C07C 227/40
[52] U.S. Cl. ............ 562/37; 562/124; 562/483; 562/485; 562/554; 562/556
[58] Field of Search ............ 562/37, 124, 433, 562/485, 554, 556

[56] References Cited

U.S. PATENT DOCUMENTS

| | | | |
|---|---|---|---|
| 4,910,336 | 3/1990 | Goodman | 562/443 |
| 5,312,980 | 5/1994 | Yonsel | 562/554 |
| 5,527,958 | 6/1996 | Yonsel | 562/554 |

FOREIGN PATENT DOCUMENTS

94/00213  1/1994  WIPO .

*Primary Examiner*—Johann Richter
*Assistant Examiner*—Jane C. Oswecki
*Attorney, Agent, or Firm*—Cushman Darby & Cushman IP Group of Pillsbury Madison & Sutro LLP

[57] ABSTRACT

The invention relates to a process for removing amino acids and/or aminosulphonic acids from preferably aqueous solutions which contain these as impurities by adsorbing the amino acids on zeolites. Solutions to which the process according to the invention can be applied are produced, for example, from the industrial synthesis of oligopeptides in which the amino acids serving as starting materials are always present in solution, sometimes to a not inconsiderable residual concentration, together with the desired end product.

11 Claims, No Drawings

PROCESS FOR SEPARATING AMINO ACIDS AND AMINOSULPONIC ACIDS THROUGH ADSORPTION ON ZEOLITES

BACKGROUND OF THE INVENTION

1. Field of the Invention

This application is based on application no. 195 35 751.5 filed in Germany on Sep. 26, 1995, the content of which is incorporated herein by reference.

The invention relates to a process for separating amino acids from preferably aqueous solutions which contain these as impurities by adsorbing the amino acids on zeolites.

2. Background Information

Solutions to which the process according to the invention may be applied result, for instance, from the industrial synthesis of oligopeptides in which the amino acids used as starting materials are still occasionally present in solution in not inconsiderable residual concentrations, together with the desired end product. A critical step during the production of pure peptides is removal of the starting products. The separation of amino acids from dipeptides is especially difficult if a process is used for preparation in which the protective group required to protect the amino groups is eliminated immediately after the coupling procedure (e.g., during peptide coupling with N-carboxylic anhydrides) and is used to couple a second unprotected amino acid. The free amino acids and free peptides present in solution in these cases often have very similar PKI values and therefore very similar dissolution behaviour. Purification by means of crystallisation is often therefore not possible, or only possible by incurring large losses. A variety of chromatographic processes, such as are described comprehensively in (1) and (2) are used for this purification procedure according to the current prior art.

In the case of partition chromatography, the different partition equilibria of amino acids and peptides between two different solvent systems (aqueous and organic) are used. If these partition equilibria are not sufficiently far apart, purification using this method is difficult to impossible.

Affinity chromatography, in which differences in the bonding strengths with specific reaction partners are used, is only suitable for very small amounts. Chromatography processes which depend on hydrophobic interactions between a support and the substances being purified (as are described for peptides and proteins in PCT/SE 93/00582)) utilise the variation of these interactions and thus bonding to the support material with the salt concentration in the eluant. The addition of non-polar organic substances is often required in this process for adequate separating power.

In comparison with the processes mentioned above, ion exchange chromatography has gained greater importance in industrial processes. The separation of amino acids and peptides here depends on differences in the isoelectric points of the substances. At acid pH's amino acids and peptides are bonded to a cation exchanger in their cationic form by ion exchange. Separation is achieved by elution with an increasing pH gradient in the eluant. At the pH which corresponds to their own isoelectric point, the individual amino acids and peptides are released and eluted.

All the chromatographic processes mentioned have the disadvantage that for substances with similar and comparable functional groups several steps are required to produce adequate purity. This means that several purification cycles are required in which relatively large losses of material cannot be avoided. In addition, the proportion of salt in the solutions is occasionally greatly increased due to elution with the addition of salts or with a pH shift. These salts, and also any other additives which are required, then have to be removed again at considerable expense.

Another process, in which separation and purification make use of differences in molecular weight and the dimensions of the molecules being separated, is gel filtration. In this case a porous matrix, generally based on organic materials, is used. Larger molecules cannot diffuse into the pores and are eluted rapidly, whereas smaller molecules are retained. The disadvantage here, however, is the high pressure which has to be applied to provide an adequate throughput.

SUMMARY OF THE INVENTION

The object of the invention is to provide a process which enables effective separation of the unconverted amino acids remaining in solution, e.g., after preparing di- or oligopeptides.

The invention provides a process for separating amino acids and/or aminosulphonic acids and products containing these or prepared from these, in particular dipeptides and/or oligopeptides in solution, characterised in that the solutions are brought into contact with a zeolite, preferably of the TA, FAU, MOR or MSI type, optionally in several steps, at a suitable pH, and the products remaining in solution are separated from the amino acids and/or aminosulphonic acids adsorbed on the zeolite.

The adsorption temperature may be between the melting and boiling points of the solvent being used, preferably between 15° and 35° C. The amino acids to be separated may be any organic compounds which contain at least one amino group and one carboxylic acid or one sulphonic acid group. Amino acids and/or aminosulphonic acids in which the amino and acid groups are linked via a $C_1$ to $C_4$ alkylene group are preferred.

If the amino acids or aminosulphonic acids contain a chiral centre, the process can be applied to both enantiomers. The amino groups may be primary, secondary or tertiary amino groups.

The amino acids and aminosulphonic acids which can be separated using the process according to the invention may also contain other functional groups such as, for example carboxyl, sulphenyl, hydroxyl, amino-thionyl, guanidine, or hetercyclic aromatic groups. These groups may optionally also carry protective groups which are conventionally used in peptide chemistry, such as, for example benzyloxycarboxyl, t-butoxycarboxyl, trifluoroacetyl, or tosyl for amino groups and guanidino or alkylesters for carboxyl groups. The process can be particularly advantageously applied to the separation of amino acids and/or aminosulphonic acids from products containing these or prepared from them, when the products also contain free amino and carboxylic or sulphonic acid groups. The process is preferably used for separating unconverted amino acids and/or aminosulphonic acids from products which are prepared by linking together two or more amino acids. Compounds in which linkage is performed via amide bonds are particularly preferred.

The process according to the invention is preferably applied to separating di- and/or tri-peptides from largely aqueous solutions, in which the amino acids or aminosulphonic acids producing the peptides are entirely or partly present.

DETAILED DESCRIPTION OF THE INVENTION

The following separations of dipeptides from α-L-amino acid contained therein may be mentioned by way of example:

Ala+Pro from Ala-Pro
Val+Pro from Val-Pro
Gly+Gln from Gly-Gln
Tyr+Arg from Tyr-Arg
Gly+Glu from Gly-Glu The following is to be regarded as an example of separating β-L-amino acids:

β-Ala+His from β-Ala-His.

The same applies to the separation of β-L-amino acids from solutions containing tripeptides:

Gly+Tyr from Gly-Gly-Tyr.

The following is mentioned as an example of the separation of a diamino-carboxylic acid, in which one amino group is protected by a trifluoroacetyl group:

ε-TFA-Lys+Pro from ε-TFA-Lys-Pro (TFA=trifluoroacetyl)

Testing the process according to the invention under conditions approximating to a practical situation demonstrates universal applicability, although amino acids may possess a number of different chemical properties.

Accordingly, peptides consisting of proteinogenic amino acids may have a) "hydrophobic" side chains: Gly, Ala, Pro, Val, and/or
b) "polar" side chains: Tyr, Gln and/or
c) "acid" side chains: Glu and/or
d) "basic" side chains: Arg, Lys as is substantiated by the amino acids listed by way of example.

According to the invention, the separation of amino acids with secondary amino groups can also be performed, such as, e.g., Sar+Ala from Sar-Ala (Sar=sarcosine).

The same also applies to the separation of aminosulphonic acids, such as, e.g.,

Ala+Tau from Ala-Tau (Tau=taurine).

Since adsorption of amino acids is possible over the entire pH range between 1 and the particular IP, no pH correction is required in solutions with the appropriate pH.

Adsorption is preferably performed at a pH less than IP (isoelectric point), while desorption preferably takes place at a pH greater than IP. If the isoelectric points of two of the amino acids or aminosulphonic acids to be removed from the solution are quite different from each other the adsorption step is optionally repeated at different pH's.

Zeolites of the FAU, MSI or Mordenite types are preferably used, these having a modulus of 15 to 200. The zeolites are known as such from the prior art.

The solution to be purified is brought into contact with the zeolites, for example, by means of direct addition of zeolite powder or moulded pellets to the solution in a container with thorough mixing. Separation of the purified, valuable product solution from the zeolite powder or moulded pellets is achieved by subsequent filtration.

Another possibility for industrial application consists of feeding the solution to be purified continuously through a column filled with zeolite powder or moulded pellets, wherein moulded pellets are preferred due to the smaller pressure drop. The free amino acids are adsorbed on zeolites in the column, while the dipeptides are almost completely contained in the discharge. The zeolite containing amino acids can, if the separated amino acids are not intended to be recovered, be regenerated by heating at temperatures between 400° and 900° C., e.g. in a rotary furnace. However, the adsorbed amino acids may also be desorbed in aqueous solutions at pH's between 10 and 12 and thus recovered. The zeolite may then be used again for purifying peptides.

Due to the favourable position of the adsorption equilibrium, it is possible to almost completely remove the amino acids or aminosulphonic acids from solution in one step, by means of the addition of an appropriate amount of zeolite. Even though in many cases, the valuable product required is also adsorbed in small amounts, the free amino acids and valuable product are still clearly separated.

This distinguishes the process according to the invention from the prior art. This arises from the high degree of efficiency, because during the removal of small amounts of side products or starting compounds from reaction solutions of valuable products being purified, of the type preferably used, the adsorption agent is not required to have any capacity for adsorbing the valuable product (here peptides), in contrast to ion exchange chromatography. The amount of adsorber required is governed only by the amounts of substances to be removed.

In contrast to gel filtration, separation is performed without the application of the high pressures which are required there due to the low loading density or loading capacity. It has also proven advantageous that, according to the invention, no salting out and no dilution of the product solution is required. The concentration of the desired products generally extends, depending on their solubility and on the concentration which can be produced by the particular process selected, from 1 wt. % to 60 wt. %, with respect to the solution containing them, in particular 4 to 30 wt. %.

The concentration of the amino acids to be removed, e.g. those used as starting compounds, at the residual concentrations found after reaction, generally range from 0.01 g/l to a value which is set by the solubility of the particular starting compound used.

If the ratio of the individual compound being separated, such as, for example, the amino acid(s), to the compound being purified in grams per liter is calculated, it is found that the process according to the invention can be successfully applied over a range from 1:1000 to 1:1.5, in particular 1:300 to 1:1.5.

Characterisation of the zeolites used corresponds to the classification according to W. M. Meier, D. H. Olson "Atlas of Zeolite Structure Types", 2nd edition Butterworth-Heinemann, London, 1987.

This applies in particular to:
Zeolite A=Zeolite TA
Zeolite DAY=Zeolite FAU
Mordenite=MOR
ZSM5=MSI The number used to label ZSM 5 types in the examples corresponds to the particular $SiO_2/Al_2O_3$ ratio.

REFERENCES

1 Ullmann's Enzyklopädie, Vol A 19, pp 168 (1991)

2 J. P. Greenstein, M. Winitiz "Chemistry of the Amino Acids" J. Wiley, New York, 1961, Vol 2, pp 1366–1511.

EXAMPLES

The examples described substantiate the ability to perform the process according to the invention.

In laboratory tests, 3 g of zeolite powder were added to each 30 ml of a solution which contained different concentrations of peptides and free amino acids and shaken for several hours until the adsorption equilibrium was well established.

After adsorption the zeolite powder was filtered off using a membrane and the supernatant liquor was analysed.

Table 1 lists the substances tested together with the analytical results and the percentage depletion produced by the adsorption step described.

TABLE

Separation of free amino acids from dipeptides or other substances

| Substance Zeolite | Concentration in initial solution (g/l) | Concentration in solution after contact with zeolite (g/l) | Percentage depletion |
|---|---|---|---|
| Ala—Pro | 285.9 | 286.5 | 0 |
| Ala | 4.0 | 0.6 | 85.0 |
| Pro | 2.4 | 0.0 | 100 |
| ZSM5/28 | | | |
| Val—Pro | 324.9 | 326.1 | 0 |
| Val | 14.1 | 2.1 | 85.1 |
| Pro | 4.5 | 0.8 | 82.2 |
| ZSM5/28 | | | |
| Gly—Gln | 89.1 | 82.0 | 7.9 |
| Gly | 5.2 | 0.2 | 96.2 |
| Gln | 2.0 | 0.2 | 90.0 |
| ZSM5/28 | | | |
| TFA-Lys—Pro | 39.1 | 39.9 | 0 |
| TFA-Lys | 3.0 | 1.0 | 66.6 |
| Pro | 2.8 | 0.1 | 96.4 |
| ZSM5/45 | | | |
| Tyr—Arg | 38.4 | 17.2 | 55.2 |
| Tyr | 0.5 | 0.3 | 40.0 |
| Arg | 4.3 | 1.2 | 72.1 |
| DAY 15 | | | |
| Gly—Gly—Tyr | 5.8 | 5.45 | 6.0 |
| Gly—Gly | 3.25 | 3.1 | 4.6 |
| Gly | 5.75 | 1.5 | 73.9 |
| Tyr | 0.3 | 0.1 | 66.6 |
| ZSM5/28 | | | |
| Gly—Glu | 8.25 | 7.8 | 5.4 |
| Gly | 9.6 | 6.1 | 36.4 |
| Glu | 5.0 | 2.4 | 52.0 |
| ZSM5/28 | | | |

What is claimed is:

1. A process for separating at least one amino acid and/or aminosulphonic acid from a solution of products containing said amino acid and/or aminosulphonic acid, and di-, tri- and oligopeptides thereof said process comprising the step of bringing said solution into contact with a zeolite at a pH which is lower than the isoelectric point of said amino acid and aminosulfonic acid so that said amino acid and/or aminosulphonic acid is adsorbed on the zeolite, separating the solution from the zeolite, and recovering the desired products from the solution wherein said zeolite is of the TA, FUA, MOR or MSI type.

2. The process according to claim 1, wherein the products include compounds which contain both amino and acid groups which are similar to amino and acid groups of the amino acids and/or aminosulfonic acids to be separated from said products.

3. The process according to claim 1 or 2, wherein the products include compounds in which at least two amino acids and/or aminosulphonic acids are linked together via an amide bond.

4. The process according to claim 1 or 2, wherein the amino acid(s) and/or aminosulfonic acids to be separated have at least two different isoelectric points, and wherein the process is carried out in at least two steps, so that at least one step is performed at a pH which is lower than the isoelectric point of each of the amino acid(s) and/or aminosulfonic acids.

5. The process according to claim 1 or 2, comprising the additional step of desorbing the amino acid(s) and/or aminosulfonic acid(s) adsorbed on the zeolite by adjusting the pH to a value greater than the isoelectric point of said amino acid(s) and/or aminosulfonic acid(s).

6. The process according to claim 1 or 2, wherein the amino and acids groups of the amino acid and/or aminosulfonic acids are linked by a $C_1$ to $C_4$ alkylene group.

7. The process according to claim 1 or 2, wherein the solution contains a di- or oligopeptide with at least one amino acid residue which has a further functional group.

8. The process according to claim 1 or 2, wherein the solution contains a di- or oligopeptide with at least one amino acid residue with a hydrophobic side chain.

9. The process according to claim 1 or 2, wherein the solution contains a di- or oligopeptide which contains at least one amino acid residue wherein an amino group is present as a primary, secondary or tertiary amine.

10. The process according to claim 1 or 2, wherein the solution contains a di- or oligopeptide which contains at least one amino acid residue wherein an amino group is present in the α-, β- and/or γ-position.

11. The process according to claim 1 or 2 which is performed batch-wise, semi-continuously or continuously.

* * * * *